United States Patent
Dunbar et al.

(10) Patent No.: US 7,074,565 B2
(45) Date of Patent: Jul. 11, 2006

(54) PREPARATION OF DNA-CONTAINING EXTRACT FOR PCR AMPLIFICATION

(75) Inventors: John M. Dunbar, Sante Fe, NM (US); Cheryl R. Kuske, Los Alamos, NM (US)

(73) Assignee: The Regents of the University of California, Los Alamos, NM (US)

( * ) Notice: Subject to any disclaimer, the term of this patent is extended or adjusted under 35 U.S.C. 154(b) by 318 days.

(21) Appl. No.: 10/439,507

(22) Filed: May 15, 2003

(65) Prior Publication Data

US 2004/0229344 A1    Nov. 18, 2004

(51) Int. Cl.
*C12Q 1/68* (2006.01)
*C12P 19/34* (2006.01)

(52) U.S. Cl. .......................... 435/6; 435/912
(58) Field of Classification Search .................... 435/6, 435/91.1, 91.2, 69.1; 536/23.1, 24.3
See application file for complete search history.

(56) References Cited

U.S. PATENT DOCUMENTS 6,350,578 B1    2/2002    Stark ..................... 435/435.72

OTHER PUBLICATIONS

Poinar et al. 1998. Science vol. 281:402-406.*
Kuske et al. 1998. Applied and Environmental Microbiology vol. 64:2463-2472.*
Hendrik N. Poinar, Michael Hofreiter, W. Geoffrey Spaulding, Paul S. Martin, B. Artur Stankiewicz, Helen Brand, Richard P. Evershed, Goran Possnert. and Svante Paabo in "Molecular Coproscopy: Dung and Diet of the Extinct Ground Sloth *Nothrotheriops shastensis*," Science. vol. 281, pp. 402-406, 1998.
S. Vasan, X. Zhang, A. Karpurniotu, J. Bernhagen, S. Teichberg, J. Basgen, D. Wagle, D. Shih, I. Terlecky, R. Bucala, A. Cerami, J. Egan, and P. Ulrich in "An Agent Cleaving Glucose-Derived Protein Crosslinks *in vitro* and *in vivo*," Nature, vol. 382, pp. 275-277, 1996.
Cheryl R. Kuske, Kaysie L. Banton, Dante L. Adorada, Peter C. Stark, Karen Hill, and Paul J. Jackson, "Small-Scale DNA Sample Preparation Method for Field PCR Detection of Microbial Cells and Spores in Soil," Appl. And Environ. Microbiol., vol. 64, No. 7, Jul. 1998, p. 2463-2472.

Yu-Li Tsai and Betty H. Olson, "Detection of Low Numbers of Bacterial Cells in Soils and Sediments by Polymerase Chain Reaction," Appl. Environ. Microbiol., vol. 58, No. 2, Feb. 1992, p. 754-757.
Yu-Li Tsai and Betty H. Olson, "Rapid Method for Separation of Bacterial DNA from Humic Substances in Sediments for Polymerase Chain Reaction," Appl. Environ. Microbiol., vol. 58, No. 7, Jul. 1992, pp. 2292-2295.
K. Smalla, N. Cresswell, L. C. Mendonca-Hagler, A. Wolters, and J. D. van Elsas, "Rapid DNA Extraction Protocol From Soil for Polymerase Chain Reaction-Mediated Amplification," J. Appl. Bact., vol. 74, 1993, p. 78-85.
L. Arlene Porteous, John L. Armstrong, Ramon J. Seidler, and Lidia S. Watrud, "An Effective Method to Extract DNA from Environmental Samples for Polymerase Chain Reaction Amplification and DNA Fingerprint Analysis", Curr. Microb., vol. 29, 1994, p. 301-307.
Jizhong Zhou, Mary Ann Bruns, and James M. Tiedje, "DNA Recovery from Soils of Diverse Composition," Appl. Environ. Microb., vol. 62, No. 2, Feb. 1996, p. 316-322.
Carol A. Kreader, "Relief of Amplification Inhibition in PCR with Bovine Serum Albumin or T4 Gene 32 Protein," Applied and Environmental Microbiology, vol. 62, No. 3, pp. 1102-1106, Mar. 1996.
Barbara J. MacGregor, Simon Toze, Elizabeth W. Alm., Richard Sharp, Cherie J. Zeimer, and David A. Stahl, "Distribution and Abundance of Gram-positive Bacteria in the Environment: Development of a Group-Specific Probe," Journal of Microbiological Methods. vol. 44, pp. 193-203, 2001.

* cited by examiner

*Primary Examiner*—Jeffrey Fredman
*Assistant Examiner*—Heather G Calamita
(74) *Attorney, Agent, or Firm*—Samuel L. Borkowsky

(57) ABSTRACT

Environmental samples typically include impurities that interfere with PCR amplification and DNA quantitation. Samples of soil, river water, and aerosol were taken from the environment and added to an aqueous buffer (with or without detergent). Cells from the sample are lysed, releasing their DNA into the buffer. After removing insoluble cell components, the remaining soluble DNA-containing extract is treated with N-phenacylthiazolium bromide, which causes rapid precipitation of impurities. Centrifugation provides a supernatant that can be used or diluted for PCR amplification of DNA, or further purified. The method may provide a DNA-containing extract sufficiently pure for PCR amplification within 5–10 minutes.

8 Claims, No Drawings

US 7,074,565 B2

PREPARATION OF DNA-CONTAINING EXTRACT FOR PCR AMPLIFICATION

STATEMENT REGARDING FEDERAL RIGHTS

This invention was made with government support under Contract No. W-7405-ENG-36 awarded by the U.S. Department of Energy. The government has certain rights in the invention.

FIELD OF THE INVENTION

The present invention relates generally to preparation of a DNA-containing-extract from an environmental sample for use with molecular biological applications such as amplification of the DNA by PCR, cloning of the DNA, enzymatic digestion of the DNA, and hybridization of the DNA with oligonucleotide probes.

BACKGROUND OF THE INVENTION

Efficient methods for extracting and purifying DNA are required for analyzing the biological composition (types of microorganisms, plant and animal cells) of environmental samples. Such analyses of environmental samples are performed for forensic investigations, for public health monitoring of pathogens in food and water supplies, for biological warfare agent detection, etc. A general procedure typically involves initial extraction of the DNA from cells and microorganisms in a soil, aqueous, or aerosol sample from the environment. This initial extraction may require steps such as incubation with detergent, freeze thawing, homogenization in a bead mill, and other steps. Subsequently, the DNA is analyzed or manipulated using one or more molecular biology techniques. One of the most common techniques applied to extracted DNA is amplification of particular DNA sequences by PCR (polymerase chain reaction), which uses extracted DNA molecules as templates from which exact DNA copies are made.

Environmental samples often contain materials that coextract with DNA and interfere in downstream molecular biology applications such as PCR. Known contaminants include metal ions, salts, complex polysaccharides, and protein-degrading enzymes. Contaminants that coextract with DNA from soil are poorly characterized and in most cases are unknown. Humic acids are known contaminants in soil that interfere with DNA quantitation (see, for example, Cheryl R. Kuske et al. in "Small-Scale DNA Sample Preparation Method for Field PCR Detection of Microbial Cells and Spores in Soil," Applied and Environmental Microbiology, vol. 64, no. 7, pp. 2463–2472, July 1998; U.S. Pat. No. 6,350,578 to Peter C. Stark et al. entitled "Method of Quantitating dsDNA," which issued on Feb. 26, 2002) inhibit PCR amplification (see, for example, Yu-Li Tsai et al. in "Detection of Low Numbers of Bacterial Cells is Soils and Sediments by Polymerase Chain Reaction," Applied and Environmental Microbiology, vol. 58, no. 2, pp. 754–757, February 2002; Yu-Li Tsai et al. in "Rapid Method for Separation of Bacterial DNA from Humic Substances in Sediments for Polymerase Chain Reaction," Applied and Environmental Microbiology, vol. 58, No. 7, pp. 2292–2295, July 1992; and Carol A. Kreader in "Relief of Amplification Inhibition in PCR With Bovine Serum Albumin or T4 Gene 32 Protein," Applied and Environmental Microbiology, vol. 62, no. 3, pp. 1102–1106, March 1996) and interfere with other molecular biology applications (see, for example, Barbara J. MacGregor et al. in "Distribution and Abundance of Gram-Positive Bacteria in the Environment: Development of a Group-Specific Probe," Journal of Microbiological Methods, vol. 44, pp. 193–203, 2001) even when present in very small concentrations.

A simple method for removing, from DNA extracts, contaminants that interfere with DNA quantitation and inhibit downstream applications such as PCR amplification is highly desirable.

Therefore, an object of the present invention is to provide a method for removing contaminants from soil samples, aqueous environmental samples, and environmental aerosol samples to obtain a purified extract for downstream applications such as PCR.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention as embodied and broadly described herein, the invention includes a method for preparing a purified DNA-containing extract from a sample of soil, water, or particle-containing aerosol taken from the environment. According to the invention a buffered, aqueous DNA-containing extract is prepared at ambient temperature from a cell-containing sample of soil, water, or particle-containing aerosol from the environment; this DNA-containing extract includes materials that interfere with PCR amplification. N-phenacylthiazolium bromide (PTB) is added to the extract, after which a soluble portion and an insoluble portion are formed, the insoluble portion including materials that interfere with PCR amplification. After removing the insoluble portion from the soluble portion, the remaining soluble portion is a purified DNA-containing extract that can be used for PCR amplification and DNA quantitation.

The invention also includes a method for preparing a purified DNA-containing extract from a sample of soil, water, or aerosol from the environment. According to the invention, a buffered phosphate-containing solution is added to a cell-containing sample of soil, water, or aerosol taken from the environment. Cells from the sample are lysed to release DNA contained therein into the buffer. Insoluble materials are separated, and N-phenacylthiazolium bromide (PTB) is added to the soluble DNA-containing portion, forming a precipitate that is separated by centrifugation, leaving a purified, DNA containing extract that can be used for PCR amplification and DNA quantitation.

DETAILED DESCRIPTION OF THE INVENTION

The present invention includes a method for preparing a DNA-containing extract from a soil sample, a liquid sample, or an aerosol sample for PCR amplification of the extracted DNA. The method involves adding N-phenacylthiazolium bromide (PTB) to cause selective, instantaneous precipitation of materials (presumably humic acids) that interfere with DNA quantitation and inhibit PCR amplification.

PTB been reported to increase the quantity of DNA recovered from sloth dung (see Hendrik N. Poinar, Michael Hofreiter, W. Geoffrey Spaulding, Paul S. Martin, B. Artur Stankiewicz, Helen Brand, Richard P. Evershed, Goran Possnert, and Svante Paabo in "Molecular Coproscopy: Dung and Diet of the Extinct Ground Sloth *Nothrotheriops shastensis*," Science, vol. 281, pp. 402–406, 1998, incorporated by reference herein). According to Poinar et al, a buffered DNA-containing extract of sloth dung is incubated with PTB for 48 hours to promote the slow reaction between PTB and proteins that are cross-linked with DNA present in the dung (see S. Vasan, X. Zhang, A. Karpurniotu, J. Bernhagen, S. Teichberg, J. Basgen, D. Wagle, D. Shih, I. Terlecky, R. Bucala, A. Cerami, J. Egan, and P. Ulrich in "An Agent Cleaving Glucose-Derived Protein Crosslinks in vitro and in vivo," Nature, vol. 382, pp. 275–277, 1996, incorporated by reference herein).

For processing soil according to the present invention, PTB is added to a soil extract, which causes the immediate precipitation of contaminants from the extract. In contrast to Poinar et al., a 48-hour incubation period is not required. Instead, PTB is added to the extract, which is then shaken for less than 5 minutes (or vortexed for a few seconds) and immediately centrifuged (30 seconds is usually sufficient) to separate the precipitate. The DNA in the supernatant in some cases can be diluted 10-fold and amplified by PCR directly. Alternatively, the DNA in the supernatant can be cleaned further by precipitation of the DNA (with sodium acetate and isopropanol, for example) followed by washing of the DNA trapped on a size selective filter.

The invention is an excellent purification method and is significantly better than existing methods. DNA from environmental samples such as soil samples is usually purified using spin columns containing SEPHADEX™ resin, or by selective binding to and subsequent elution from glass beads or DNA-binding membranes. Purification with a SEPHADEX™ column requires column preparation time, centrifugation of the column to remove excess buffer, and a second centrifugation step for passing DNA through the column. Soils with high humic acid concentrations may require passage through several columns before the DNA is purified sufficiently for PCR and typically the DNA must be crudely quantified and diluted prior to purification to avoid overloading a column. Purification of DNA using glass bead binding, or binding to silica membranes, typically results in loss of at least 20% of the starting DNA quantity (e.g. FastDNA™, Spin kit-Bio 101, Vista, Calif.; Mo Bio soil DNA isolation kit—Mo Bio, Solana Beach Calif.), is not very effective for purifying dilute solutions of DNA. Furthermore, these methods are much more time consuming than the method of the present invention, and are also more expensive in terms of labor and materials. Use of PTB according to the invention can, in most cases, replace existing purification methods or can be used in conjunction with existing methods. According to the invention, PTB can be used to purify DNA from a variety of environmental samples, including soil samples, aqueous samples, and aerosols. The following EXAMPLES of the invention describe details for preparing purified extracts from a soil sample (EXAMPLE 1), from a liquid sample such as river water (EXAMPLES 2 AND 3), and from an environmental aerosol sample (EXAMPLE 4). All EXAMPLES were performed at ambient temperature, which for the purposes of the invention is from about 60 degrees Fahrenheit to about 80 degrees Fahrenheit.

EXAMPLE 1

Preparation of a DNA extract from a soil sample. Soil (0.5 g) is added to a 2 ml tube containing buffer (100 mM phosphate buffer pH 7.2 with 0.01% Tween 80 (a non-ionic detergent) and zirconium-silica beads (0.1 to 1 mm in diameter). The tube is shaken for 1.5 minutes on a commercially available shaker and then centrifuged for 1 minute to pellet heavy particles. The supernatant containing DNA and other soluble compounds is transferred to a sterile 1.5 ml tube, and 1M PTB was added at a 1:10 ratio (10 µl of 1M PTB per 100 µl supernatant). The PTB-containing extract was mixed by vortexing for 3 seconds and immediately centrifuged for 20 seconds to pellet precipitated material. The DNA was precipitated with 0.1 volumes of sodium acetate and 0.6 volumes of isopropanol, washed with ice-cold 70% ethanol, and resuspended in buffer (5 mM Tris [hydroxymethyl]ammoniumethane pH 8).

EXAMPLE 2

Preparation of a DNA extract from a liquid sample. A liquid sample (eg. 1 ml of river water) is added to a 2 ml tube containing buffer (e.g. 10 mM Tris[hydroxymethyl]ammoniumethane, pH 8, 1 mM EDTA, with or without detergent) and zirconium-silica beads (0.1 to 1 mm in diameter). The tube is shaken for 1.5 minutes on a commercially available instrument, then centrifuged for 30 seconds to pellet heavy particles. The supernatant (containing DNA and other soluble compounds) in the tube is transferred to a sterile 1.5 ml tube, and PTB is added as described in EXAMPLE 1 (this provides a concentration of PTB is about 100 mM). The DNA is concentrated by precipitation with 0.1 volumes of sodium acetate and 0.6 volumes of isopropanol, washed with 10 mM Tris[hydroxymethyl]ammoniumethane pH 8 in a size selection filter (eg. Microcon YM 100), and resuspended in buffer (10 mM Tris[hydroxymethyl]ammoniumethane pH 8).

EXAMPLE 3

Preparation of a DNA extract from a liquid sample. A liquid sample (eg. 100 ml of tap water from a public water utility concentrated by filtration to 1 ml) is added to a 2 ml tube containing buffer (e.g. 10 mM Tris[hydroxymethyl] ammoniumethane, pH 8, 1 mM EDTA, with or without detergent) and zirconium-silica beads (0.1 to 1 mm in diameter). The tube is shaken for 1.5 minutes on a commercially available instrument, then centrifuged for 10 seconds to pellet heavy particles. The supernatant (containing DNA and other soluble compounds) in the tube is transferred to a sterile 1.5 ml tube, and PTB is added as described in EXAMPLE 1 (this provides a concentration of PTB is about 100 mM). The DNA is concentrated by precipitation with 0.1 volumes of sodium acetate and 0.6 volumes of isopropanol, washed with 10 mM Tris[hydroxymethyl]ammoniumethane pH 8 in a size selection filter (eg. Microcon YM 100), and resuspended in buffer (10 mM Tris[hydroxymethyl]ammoniumethane pH 8).

EXAMPLE 4

Preparation of a DNA extract from an aerosol sample. An aerosol filter (a PM2.5, 47 mm Teflon filter from Washington, D.C.) is placed in a 50 ml tube containing 30 ml of buffer (100 mM phosphate buffer pH 7.2 with 0.01% Tween 80) and shaken for 15 minutes to remove particulate matter (including microbial cells) from the filter surface. The tube is centrifuged for 5 minutes at 4000 rcf to pellet the particulate matter. Excess liquid (about 29.5 ml) is removed. The particulate matter is resuspended in 1 ml of buffer, transferred to a sterile 2 ml screw-cap tube containing zirconium-silica beads (0.1 to 1 mm in diameter). The tube is shaken for 1.5 minutes on a commercially available instrument, then centrifuged for 10 seconds to pellet heavy particles. The supernatant is transferred to a sterile 1.5 ml tube, and PTB is added as described in the invention disclosure. The DNA is concentrated by precipitation with $\frac{1}{10}$ volume of sodium acetate, 0.6 volumes of isopropanol, and linear polyacrylamide (Gen-Elute LPA, Sigma Chemical Co.). The DNA is washed with ice-cold 70% ethanol and resuspended in buffer (10 mM Tris[hydroxymethyl]ammoniumethane pH 8).

The invention has been used to remove interfering/inhibitory materials from a wide range of soil and aerosol samples obtained from across the country. Soil samples were obtained from New Mexico, Colorado, North Carolina, California, New York, Norway, Wisconsin, Ohio, and Minnesota. PM2.5 aerosol samples from the EPA ambient air quality monitoring program were obtained from state air monitoring agencies in Miami, Florida; Nashville, Tennessee; Washington D.C.; New York, New York; Chicago, Illinois; Denver, Colorado; Phoenix, Arizona; Houston and Dallas, Texas; San Diego, San Francisco, and Los Angeles, California; and Seattle, Washington. The samples varied dramatically in total abundance of biological material (ranging, for example, from a few microbial cells to a trillion cells), abundance of humic acids, pH, amount of clay present, and mineral content.

In summary, the invention provides a more rapid, more efficient, and less expensive method for preparing DNA-containing extracts that are ready for PCR amplification than existing methods. Whereas other methods require many hours and sometimes days, the method of the invention may provide a DNA-containing extract ready for PCR amplification within 1 hour and in many cases within 5 to 10 minutes.

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for preparing a purified DNA-containing extract from a sample of soil, water, or particle-containing aerosol taken from the environment, comprising the steps of:
   (a) preparing a buffered, aqueous DNA-containing extract at ambient temperature from a sample of soil, water, or particle-containing aerosol from the environment, the sample comprising DNA-containing cells, the DNA-containing extract comprising materials that interfere with PCR amplification; and
   (b) combining N-phenacylthiazolium bromide (PTB) with the aqueous DNA-containing extract at ambient temperature and thoroughly mixing the combination until a precipitate forms and then removing the precipitate, wherein step (b) is performed within a time period of less than an hour.

2. The method of claim 1, wherein the buffered extract of step (a) comprises phosphate.

3. The method of claim 2, wherein the buffered extract of step (a) further comprises detergent.

4. The method of claim 1, wherein step (a) comprises placing the sample, glass beads, and a buffered solution into a tube, shaking the tube to lyse cells and release DNA into the buffered solution, and then centrifuging the tube to produce a solid and a supernatant comprising the aqueous DNA-containing extract.

5. The method of claim 1, wherein step (b) comprises, within a time period of less than an hour, adding enough PTB to the aqueous DNA-containing extract to provide a PTB concentration of about 100 mM, thoroughly mixing the resulting PTB-containing combination, centrifuging the mixture to provide a supernatant comprising a DNA-containing extract having a sufficient purity for PCR amplification.

6. The method of claim 5, wherein step (b) is performed within a time period of less than 5 minutes.

7. A method for preparing a purified DNA-containing extract from a sample of soil, water, or aerosol from the environment, comprising providing a sample of soil, water, or aerosol from the environment, the sample comprising DNA-containing cells; adding a buffered phosphate-containing solution to the sample at ambient temperature and lysing cells from the sample to release DNA contained therein to produce a soluble DNA-containing portion and an insoluble portion; separating the soluble portion from the insoluble portion; and within a period of time of less than one hour adding N-phenacylthiazolium bromide (PTB) to the soluble portion and thoroughly mixing the combination to form a precipitate and separating the precipitate by centrifugation to provide a DNA-containing extract sufficiently pure for DNA amplification by PCR.

8. The method of claim 7, wherein the DNA-containing extract sufficiently pure for DNA amplification by PCR is produced within five minutes of addition of N-phenacylthiazolium bromide.

* * * * *